United States Patent [19]
Jeromin et al.

[11] Patent Number: 5,527,974
[45] Date of Patent: Jun. 18, 1996

[54] PROCESS FOR THE PURIFICATION OF GLYCEROL WATER

[75] Inventors: Lutz Jeromin, Hilden; Wilhelm Johannisbauer, Erkrath; Stefan Blum, Langenfeld; Reinhold Sedelies, Schifferstadt; Heinrich Moormann, Duesseldorf; Bernd Holfoth, Langenfeld; Juergen Plachenka, Mettmann, all of Germany

[73] Assignee: Henkel Kommanditgesellschaft auf Aktien, Duesseldorf, Germany

[21] Appl. No.: 284,531

[22] Filed: Sep. 29, 1994

[30] Foreign Application Priority Data

Feb. 5, 1992 [DE] Germany ............ 42 03 157.5

[51] Int. Cl.⁶ .................................................. C07C 31/22
[52] U.S. Cl. .................................................. 568/869
[58] Field of Search ................................... 568/869

[56] References Cited

U.S. PATENT DOCUMENTS

| | | | |
|---|---|---|---|
| 3,803,031 | 4/1974 | Keller | 210/32 |
| 4,986,918 | 1/1991 | Breslau et al. | 210/652 |
| 4,990,695 | 2/1991 | Buenemann et al. | 568/869 |

FOREIGN PATENT DOCUMENTS

| | | |
|---|---|---|
| 0358255 | 3/1990 | European Pat. Off. . |
| 0451721 | 10/1991 | European Pat. Off. . |
| 2263996 | 10/1975 | France . |
| 0231066 | 12/1985 | Germany ............ 568/869 |
| 0547765 | 4/1974 | Switzerland . |
| 1216176 | 3/1986 | U.S.S.R. . |

OTHER PUBLICATIONS

J. Am. Oil Chemists Soc., 1979, pp. 812 A–819 A.
CA84:46428, Schmidt et al, 1975.

Primary Examiner—Rebecca Cook
Attorney, Agent, or Firm—Wayne C. Jaeschke; John E. Drach; Henry E. Millson, Jr.

[57] ABSTRACT

The glycerol water (sweet water) accumulating in the high-pressure hydrolysis of natural fats and oils with steam into fatty acid and glycerol is continuously purified. Fats larger than 100 μm in diameter are separated from the aqueous phase in a plate-type phase separator and are returned to the high-pressure hydrolysis process. The aqueous phase thus prepurified is passed through a cross-flow filtration membrane, more particularly a microfiltration membrane, and the concentrate is returned to the entrance of the plate-phase separator. Large product streams of glycerol water can be purified continuously, effectively and particularly economically despite frequent changes of provenance.

8 Claims, 7 Drawing Sheets

PROCESS FOR THE PURIFICATION OF GLYCEROL WATER

BACKGROUND OF THE INVENTION

This invention relates to a continuous process for the purification of glycerol water (sweet water) accumulating in the high-pressure hydrolysis of natural fats and oils with steam into fatty acid and glycerol.

For the production of glycerol, natural oils and fats are hydrolyzed with water under pressures of up to 100 bar and at temperatures of 100° to 250° C. Two phases are obtained, namely a light phase which contains the fatty acids and a heavy phase which consists essentially of glycerol and water and which is called "sweet water".

The need for high-purity glycerol requires removal of the impurities present in the natural fats and oils and in the sweet water. These impurities are naturally present in the renewable fats and oils while other impurities are added at the recovery stage (harvest, slaughterhouse). Accordingly, hydrolysis is preceded by purification of the oils and fats in a complicated process.

After the high pressure hydrolysis of the oils and fats into glycerol and fatty acids, a mixture of two phases is obtained, namely a heavy glycerol/water phase and a light fatty acid phase which is removed from the mixture by gravity separation. However, small quantities of fatty acids and other fats cannot be prevented from being removed with the glycerol/water phase. The small quantities of secondary products which are formed during the hydrolysis, for example diglycerides and monoglycerides, and triglycerides are also present in the sweet water. The impurities in the glycerol water are collectively referred to as matter of organic non-glycerol (MONG).

After phase separation, the glycerol water phase is restored to normal pressure, the organic impurities being highly emulsified in the process. The emulsion is concentrated by evaporation to 75–85% glycerol water and is then worked up into pure glycerol. The impurities lead during concentration to the formation of crusts on the heat exchanger surfaces and hence to considerable losses of performance. The reductions in capacity during concentration caused by the relatively long residence times, the product losses and the need for further purification steps are further disadvantages of the prior art.

A review of known processes for the production of pure glycerol from glycerol water (sweet water) can be found in J. Am. Oil Chemists Soc., 1979, pages 812 A–819 A.

The purification of glycerol water is problematical above all in two respects. Firstly, large product streams in excess of 20 m³/h have to be continuously processed. Secondly, the product used for the hydrolysis of fats frequently changes in industrial-scale processes. Thus, palm oil, palm kernel oil, beef tallow, rapeseed oil, fish oil and other oils and fats are processed. The impurities in the glycerol water reflect the C-chain distribution of the starting products so that, for example, filtration cannot be carried out continuously on account of the different solidification points of the emulsified MONG phase.

Accordingly, the problem addressed by the present invention was to provide a particularly economic process of the type mentioned at the beginning which would be capable of purifying large product streams of glycerol water continuously, effectively and economically despite frequent changes of provenance.

DESCRIPTION OF THE INVENTION

According to the invention, the solution to this problem is characterized in that fats larger than 100 µm in diameter are removed from the aqueous phase by means of a plate-type phase separator and are returned to the high-pressure hyrolysis process, the aqueous phase thus prepurified is passed through a crossflow filtration membrane, more particularly a microfiltration membrane, and the concentrate is returned to the entrance of the plate-type phase separator. The permeate obtained is concentrated by evaporation in following steps.

According to the invention, the glycerol water is purified in two stages by means of throughflow apparatus with no moving parts. The particular feature of crossflow membrane filtration, namely reducing the formation of coatings on the membrane surface by shear forces applied by the liquid lowing over, is very important in this case on account of the MONG component which can lead to blockage of the membrane.

In one embodiment of particular advantage for continuous operation, the filtration membrane is periodically cleaned by backwashing with alkali hydroxide. Hitherto, the known principle of backwashing membranes has hitherto been applied to remove coatings of suspended ingredients. Pressure is applied to a completely coated membrane on the permeate side to force permeate back through the membrane. The coating is blown off and discharged on the concentrate side. According to the invention, this step is correspondingly applied to the gel-like high-viscosity coatings consisting of MONG. At the beginning of the backwashing phase, the production circuit is shut off and alkali hydroxide, for example sodium hydroxide, is subsequently introduced into the membrane under pressure from the permeate side. The coatings are saponified and thus become soluble in water.

The used backwashing liquid is preferably collected in a container, the membrane is rinsed with acid after backwashing, the rinsing liquid is also collected in the container, so that the soaps formed therein are decomposed, and the contents of the container are finally returned to the entrance of the plate-type phase separator.

It is of advantage, particularly for continuous operation, to keep the flow of permeate through the membrane constant by changing the transmembranal pressure. Accordingly, any reduction in the flow of permeate can be counteracted by an increase in pressure on the concentrate side. In the case of products which form a surface layer, this adjustment can only be continued until an upper pressure limit is reached. Accordingly, it is proposed that backwashing should begin when a predetermined transmembranal pressure is exceeded. Adjustment of the permeate flow and the initiation of backwashing can readily be automated.

A particularly clear, unclouded, purified glycerol water is obtained when membrane filtration is carried out at temperatures below 50° C. and, more particularly, at temperatures below 40° C.

Another embodiment of the invention is characterized by the use of a backwashable membrane, more particularly a ceramic membrane, preferably of graphite or $Al_2O_3$, which has a pore diameter of 0.5 to 2 µm. The membrane is compact, shows high chemical mechanical resistance and is therefore particularly suitable for use on an industrial scale. The conflicting requirements of achieving high permeate flows for high MONG retention and good purification behavior can be satisfied by the pore diameters mentioned above.

The backwashing cycles of the membrane can be extended by passing the aqueous phase prepurified in the plate-type phase separator through a fiber bed separator, returning the light phase obtained to the high pressure hydrolysis process and feeding the heavy phase to the membrane filtration stage of which the concentrate is delivered to the entrance of the fiber bed separator.

If impurities capable of causing irreversible blockage of the fiber bed separator or the membrane are expected to occur, the filtration membrane may be preceded by an adsorption unit in another advantageous embodiment of the invention. The impurities can be adsorbed, for example, on polyethylene granules.

BRIEF DESCRIPTION OF THE DRAWINGS

Examples of embodiment and test results are presented in the following with reference to the accompanying drawings, wherein.

Figure 1:
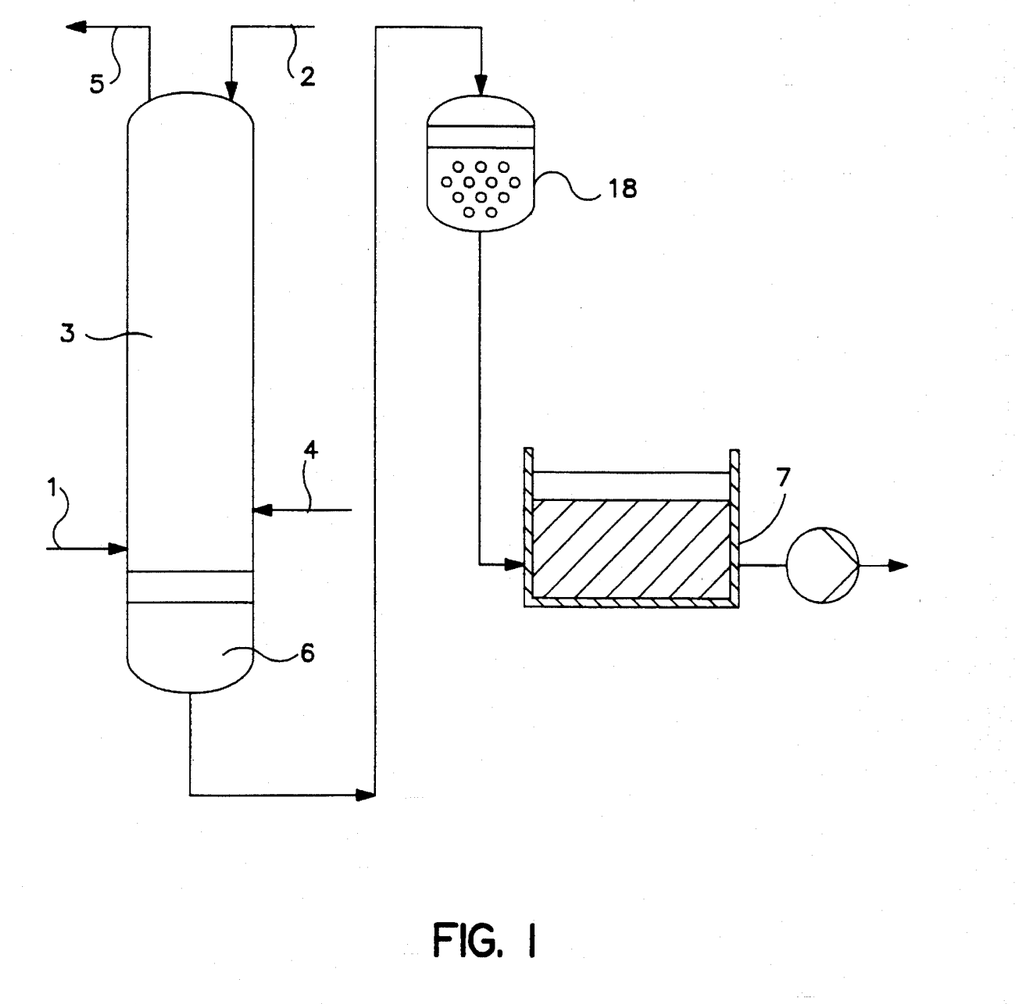
FIG. 1 diagrammatically illustrates a standard installation for the continuous hydrolysis of fats.

The glycerol-containing aqueous phase to be purified may be obtained, for example, from an installation for the high-pressure hydrolysis of natural fats and oils (triglycerides) with water into fatty acid and glycerol. A typical installation is shown in FIG. 1. Fat/oil 1 and water 2 are fed in at the foot or head of a hydrolysis column 3. The reactor is heated with high-pressure steam 4 at approx. 250° C./75 bar. The fatty acid 5 formed is removed at the head of the column. A glycerol water/MONG mixture 6 collects in the sump from which it is removed, expanded to normal pressure in the vessel 18 and collected in a separator 7. The impurities (MONG) of the glycerol water contain 80% free fatty acids, 15% fatty acid esters and 5% other impurities.

For purification, the crude glycerol water is subjected to membrane filtration after preliminary purification in a plate-type separator. The concentrate accumulating during the membrane filtration process is returned to the entrance of the plate-type separator. MONG separated therefrom is returned to the high-pressure hydrolysis process.

Figure 2:
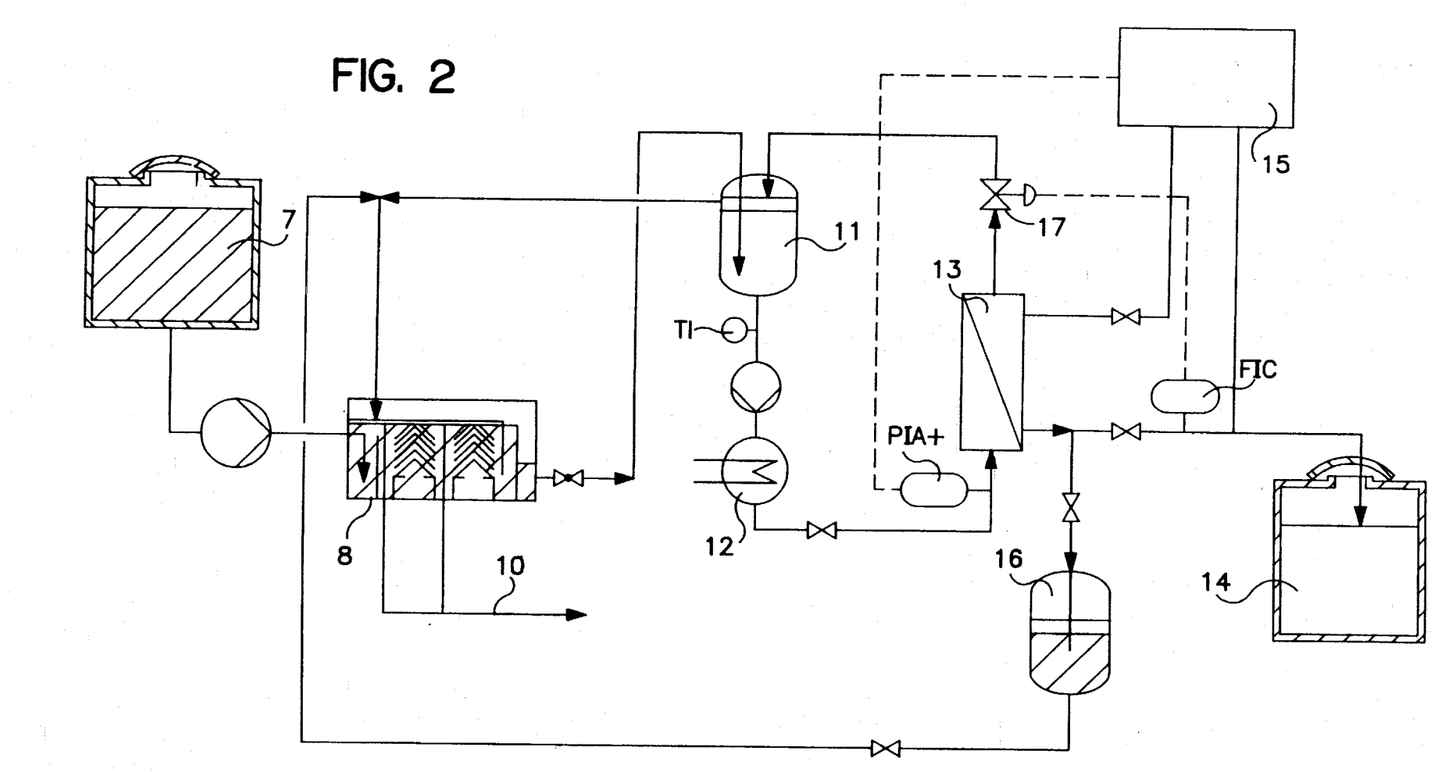
FIG. 2 diagrammatically illustrates an installation corresponding to one embodiment of the invention.

An installation suitable for carrying out the process according to the invention is schematically illustrated in FIG. 2. The glycerol water to be purified, which is collected in a receiver 9, is pumped into a plate-type phase separator 8. The impurities (MONG) are returned through a pipe 10 to the high-pressure hydrolysis process and the prepurified glycerol water flows into a separator 11. Phase separation again takes place in the separator 11 and the light phase is delivered to the plate-type phase separator 8. The heavy phase is delivered to a microfiltration module 13 via a heater/cooler 12 used to establish the operating temperature of the membrane filtration process. The concentrate flows back into the separator 11 while the permeate is collected in a receiver 14. In addition, a controller 15 and a vessel 16 for soap decomposition are provided for the backwashing of the membrane module 13. The installation also comprises means for regulating the permeate flow (FIC, valve 17) and for adjusting the transmembranal pressure by partial throttling of the retentate stream (PIA).

Figure 3:
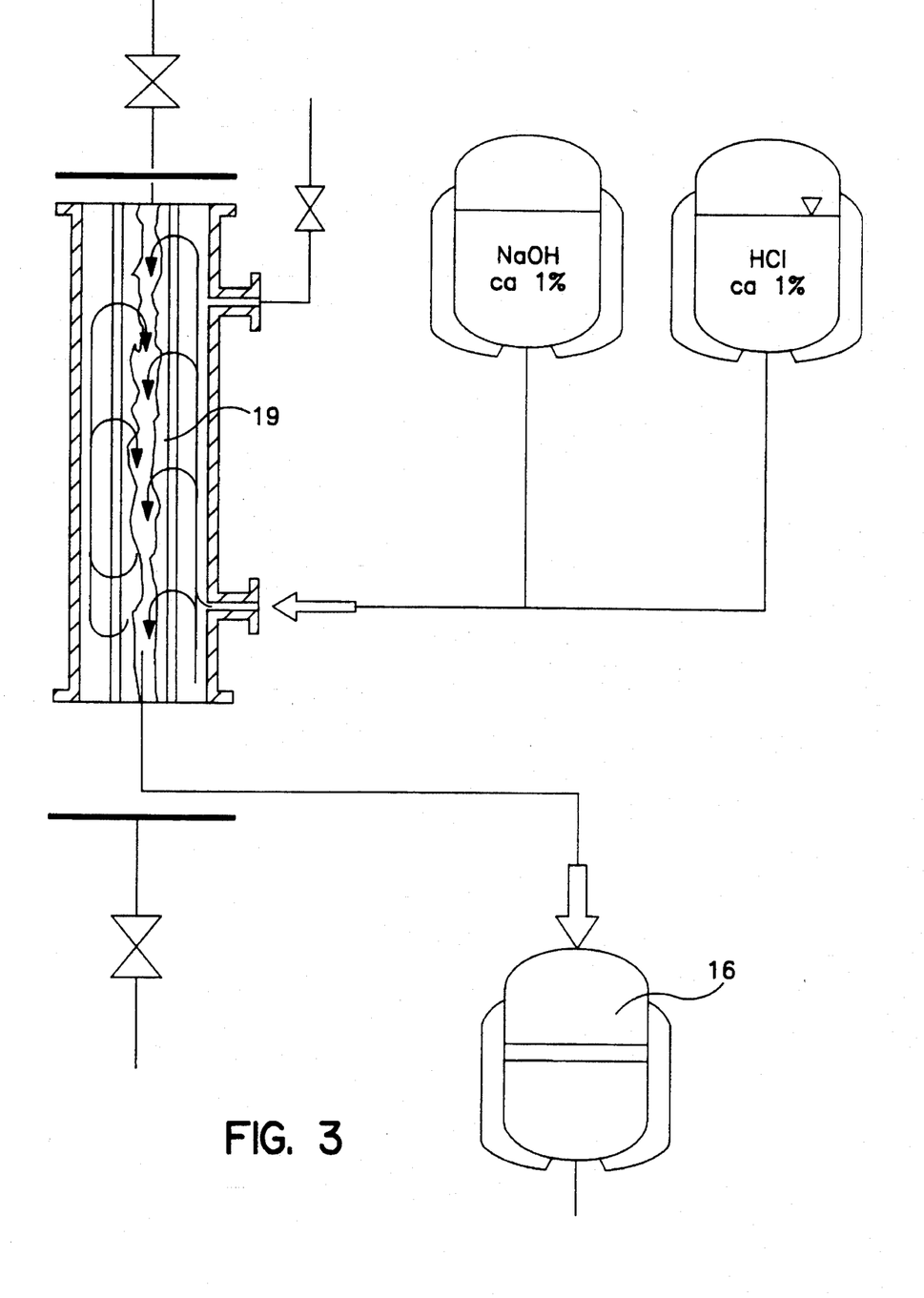
FIG. 3 is a schematic illustration explaining the mode of action of membrane backwashing.

The backwashing of the membrane module is illustrated in FIG. 3. The membrane 19 is washed first with sodium hydroxide and then with acid on the permeate side. The washing liquid with the coating removed from the inside of the membrane 19 is collected in a vessel 16.

Figure 4:
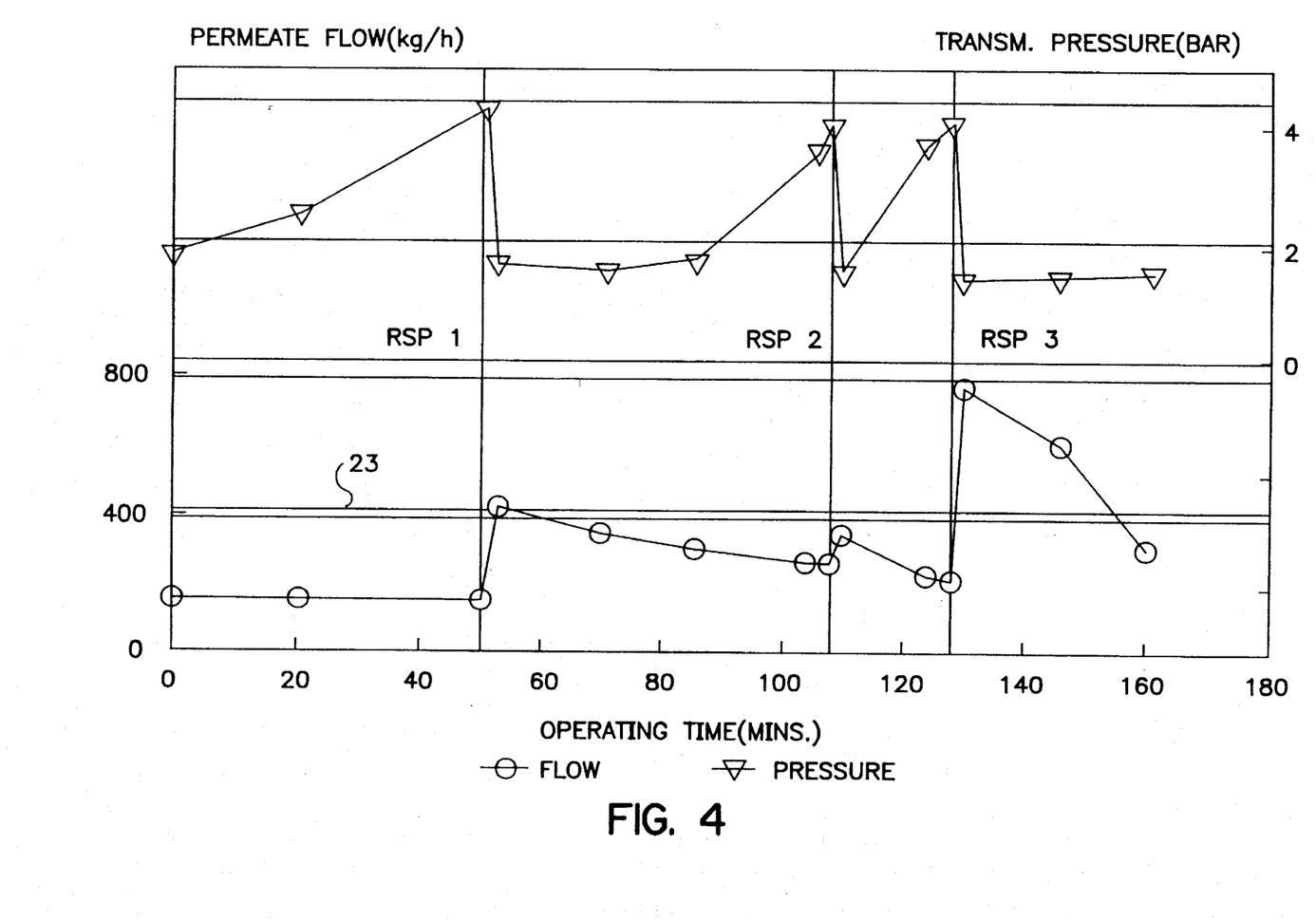
FIG. 4 shows the average permeate flow using an $AlO_3$ membrane.
Figure 5:
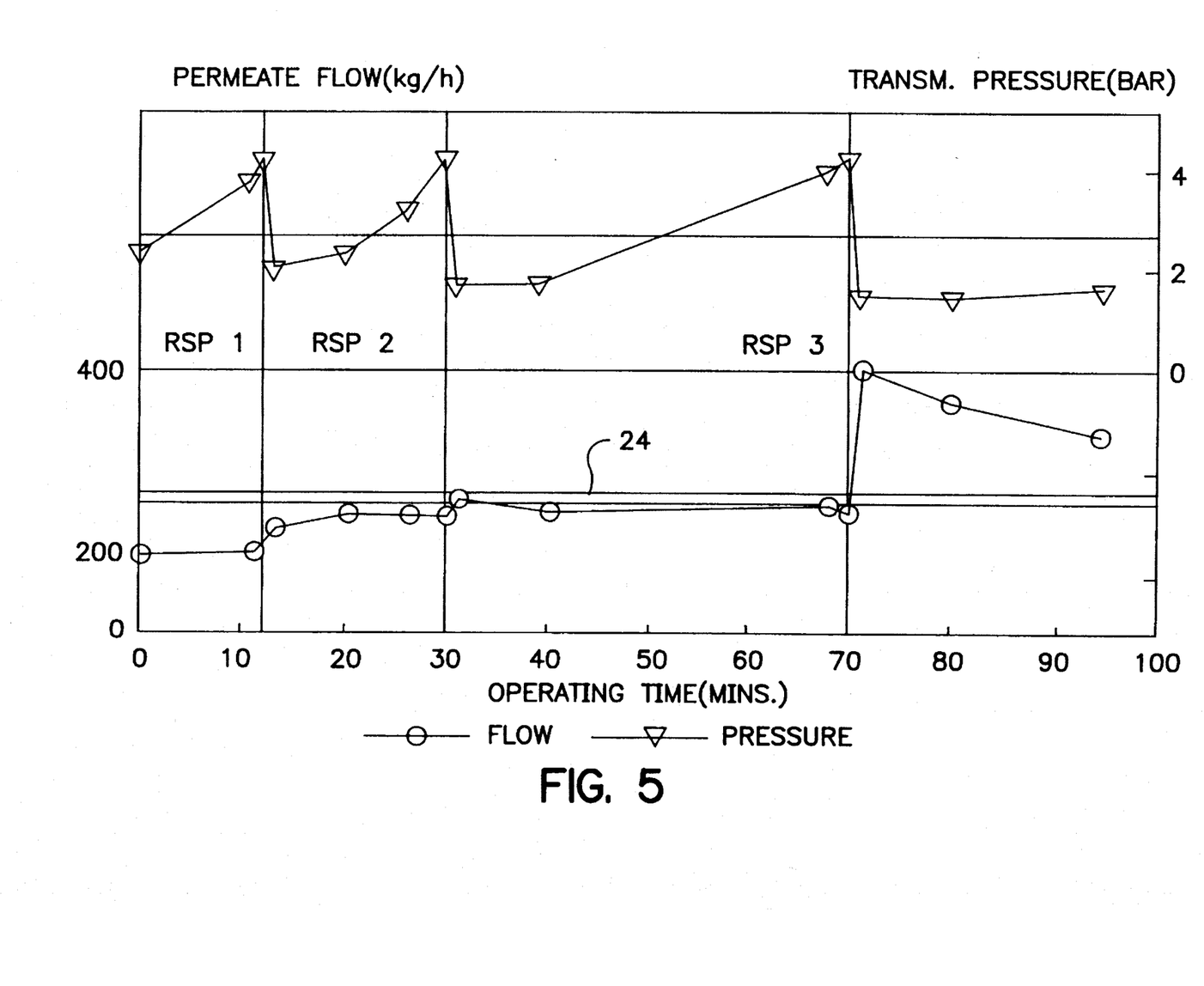
FIG. 5 shows the permeate flow obtained with 40% glycerol water.

FIGS. 4 and 5 show test results obtained with the process according to the invention. The tests were carried out in the installation shown in FIG. 2. The starting material was glycerol water containing 15% glycerol from the high-pressure hydrolysis process. It was brown and cloudy in consistency. The results shown in FIG. 4 were obtained with an $Al_2O_3$ membrane having a pore diameter of 0.8 μm for a membrane area of 0.2 m$^2$ at a temperature of 70° C. The line 23 characterizes the average permeate flow of 414 kg/h, corresponding to 2,071 kg/m$^2$ h.

The initials RSP stands for the backwashing cycles. Backwashing was initiated when the transmembranal pressure limit of 4 bar was exceeded. The backwashing time was 10 seconds for NaOH (aq. 1%) and for $H_2SO_4$ (aq. 1%). Immediately after backwashing, permeate flows of up to 4,000 l/m$^2$ h were measured for a transmembranal pressure difference of 1.6 bar, falling to 1,000 l/m$^2$ h over a period of 30 minutes. By controlling backwashing, the permeate flow was kept constant for another 30 minutes until backwashing began. Thereafter, extremely high flows were again measured. An average permeate flow of approx. 2,000 l/m$^2$ h was achieved in this way. This required approximately one backwash per hour. Through the integrated soap decomposition with recycling to the plate-type phase separator, the $Na_2SO_4$ content in the permeate was less than 50 ppm. The permeate was clear and yellow in color, but became slightly cloudy on cooling. This effect did not occur at relatively low operating temperatures (32° C.).

The values shown in FIG. 5 were obtained with 40% glycerol water at an operating temperature of 32° C. After the first and second backwashes, the required permeate flow was 180 kg/h and, after the third backwash, 300 kg/h. The average flow of 214 kg/h, corresponding to 1,070 kg/m$^2$ h, is shown as a line 24. In this case, an average of two backwashes per hour were required.

Two measured quantities were available for determining the retention of the membrane, namely: particle size distribution and turbidity. The particle size x90, which indicates the diameter below which 90% of the particles lie, serves as the significant value for particle size distribution.

The particle size x90 was approximately 2.5 μm at 70° C., irrespective of the input, the permeate being particle-free at 30° C.

Turbidity was determined relative to water, water being assumed to have an turbidity of 0%. The permeate obtained at 70° C. had a turbidity of 5% while the permeate obtained at 30° C. had a turbidity of 1.5% which is attributable to its yellow coloration.

Figure 6:
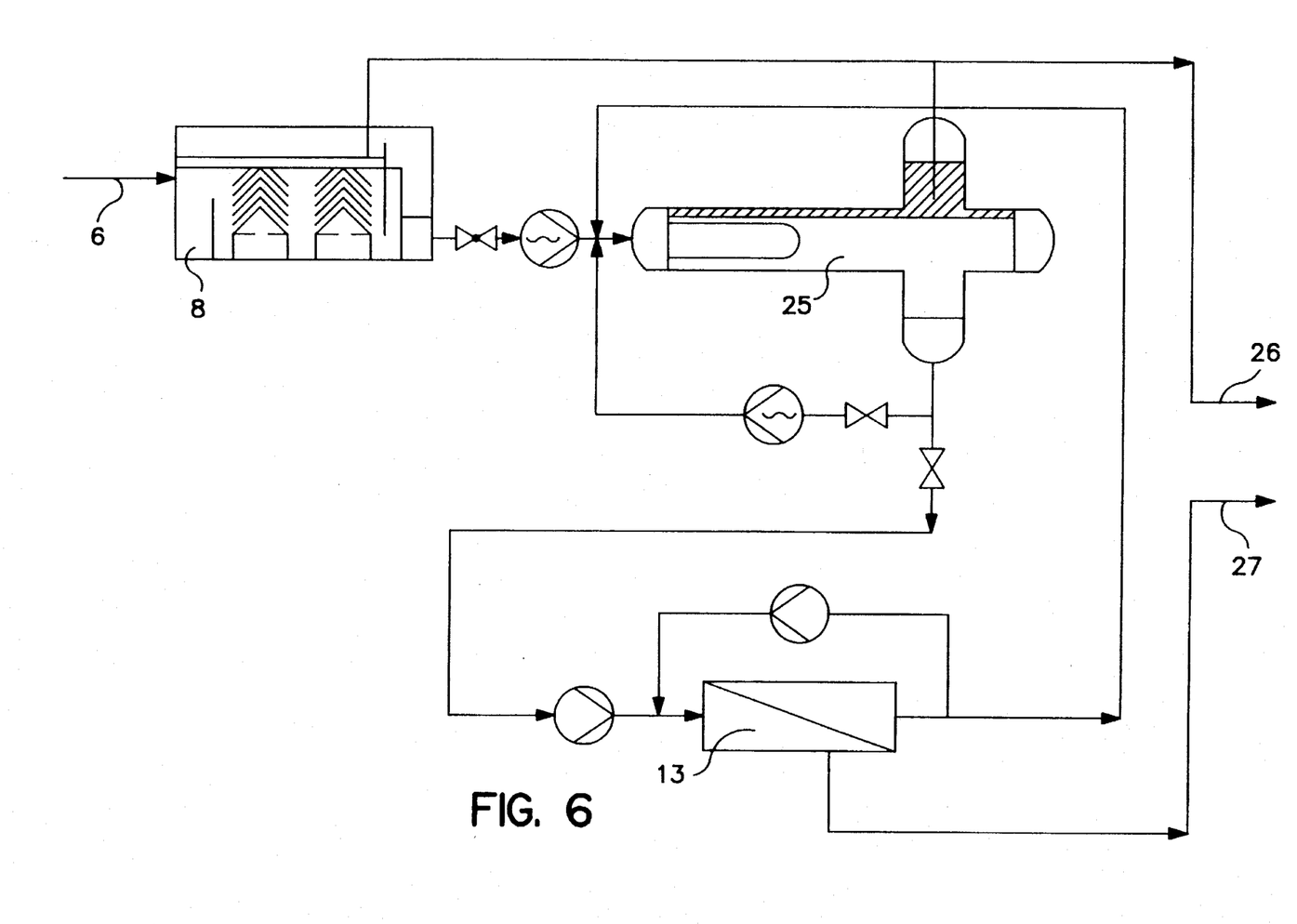
FIG. 6 diagrammatically illustrates an installation corresponding to another embodiment of the invention.
Figure 7:
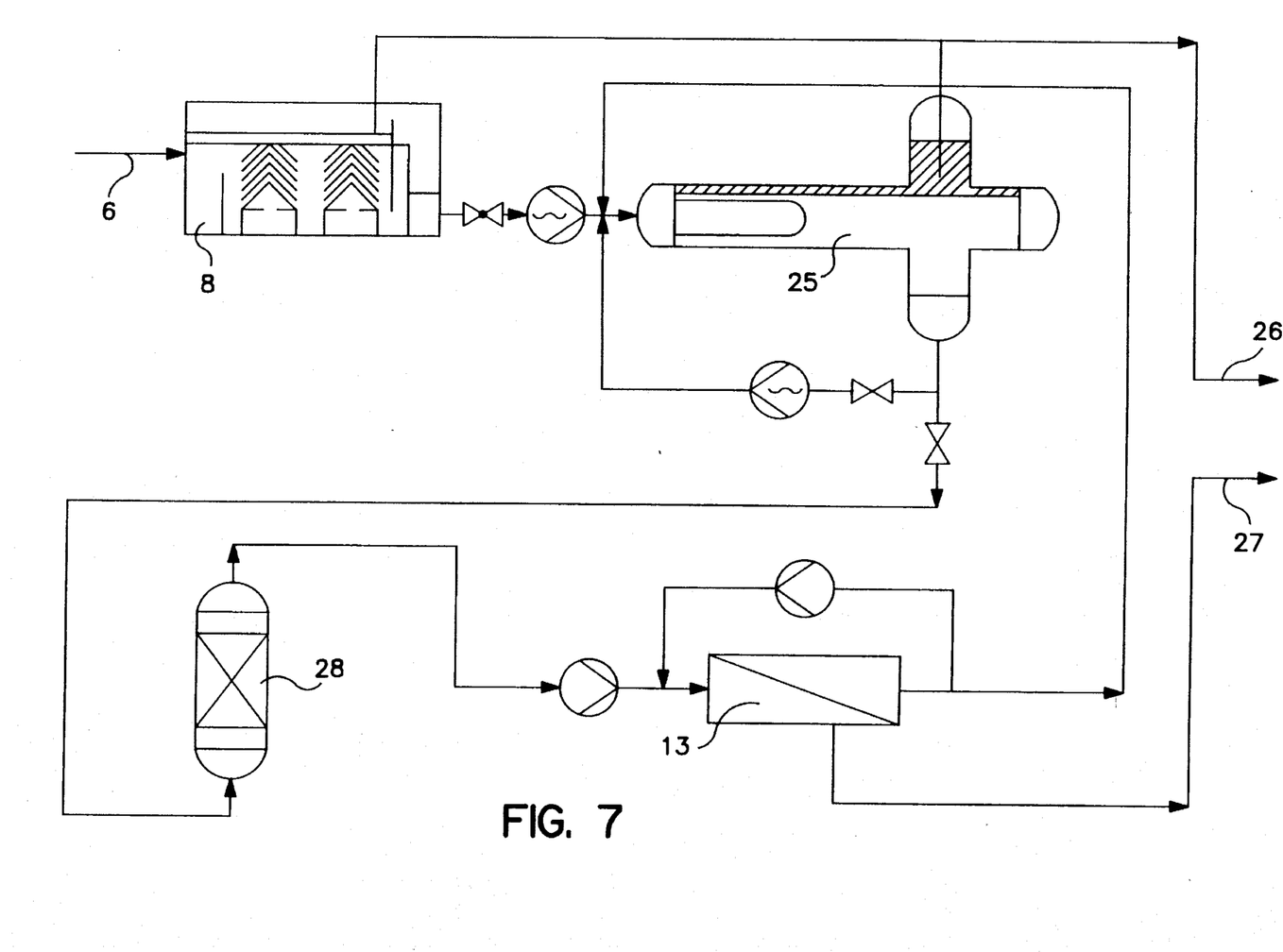
FIG. 7 diagrammatically illustrates an installation corresponding to a modification of this other embodiment.

In another embodiment of the invention, a plate-type phase separator 8, a fiber bed separator 25 and a microfiltration module 13 are arranged in series. Corresponding installations are shown in FIGS. 6 and 7 where the same elements are again noted by the same reference numerals. MONG is denoted by the reference numeral 26 and the purified glycerol water by the reference numeral 27.

This process is based on step-by-step hydrolysis of the emulsion in throughflow apparatus with no moving parts.

Each stage is used for preliminary purification of the following process. Drops and particles larger than 100 μm in diameter are removed in the plate-type phase separator in which a continuous MONG phase can be creamed off. In addition, coarse heavy soil particles can be separated off and removed at the base. The intermediate phase enters the fiber bed separator (coalescence separator) of which the central elements form tightly wound fiber candles.

The constituent material of the fibers can be optimally adapted to the product properties. In addition, the thickness of the fibers can be varied.

The choice of the fibers is determined by the product properties, but especially by the viscosity which is both highly dependent on temperature and varies distinctly for the various products (C chain length). For example, a 5 μm candle can produce good demulsification at 70° C. in the case of glycerol water from the hydrolysis of vegetable oils ($C_8$–$C_{12}$), although increasing contents of tallow, rapeseed oil or fish oil ($C_{18}$–$C_{22}$) result in gradual blockage at the same temperature. The blockage can be eliminated by increasing the temperature. This is utilized in a pressure loss control system. The pressure loss through the fiber candle is used as a control qantity while the temperature of the glycerol water to be purified is used as a controlled variable.

It is known that the fiber candles require a certain pressure loss for optimal operation. The exact pressure loss can be adjusted for each glycerol water by exact control of the temperature.

With correct operation, two phases leave the coalescence separator 2, namely a lighter MONG phase and a purified glycerol water/MONG residual emulsion which cannot be completely demulsified even with extremely fine fibers. This phase is delivered to the microfiltration stage.

In the case of impurities which can cause irreversible blockages in the fiber bed separator 25 or the membrane (for example polyethylene from slaughterhouse sacks), an adsorption column 28—filled with polyethylene granules in the above-mentioned case—may be integrated to adsorb the impurities (FIG. 7).

List of Reference Numerals

1 Fat/oil
2 Water
3 Hydrolysis column
4 High-pressure steam
5 Fatty acid
6 Glycerol water/MONG mixture
7 Separator
8 Plate-type phase separator
9 Receiver
10 Pipe
11 Separator
12 Heater/cooler
13 Microfiltration module
14 Receiver, permeate tank
15 Controller
16 Vessel
17 Valve
18 Vessel
19 Membrane
23 Line
24 Line
25 Fiber bed separator
26 MONG
27 Purified glycerol water
28 Adsorption column

What is claimed is:

1. A process for purifying a glycerol-water-fatty matter droplets mixture obtained from the hydrolysis reaction of a fat or an oil comprising the steps of: (1) passing said glycerol-water-fatty matter droplets mixture through a plate-type phase separation zone thereby separating fat particles having a diameter greater than 100 μm and forming a prepurified liquid phase; (2) returning said fat particles to said hydrolysis reaction; (3) passing said prepurified liquid phase from step (1) through a crossflow filtration membrane filtration zone wherein the crossflow filtration membrane in said membrane filtration zone has a pore diameter of 0.5 to 2.0 μm at a temperature below 50° C., to form a retentate which is returned to the input of said plate-type separation zone and a permeate comprised of glycerol and water (4) backwashing the membrane filter in said crossflow filtration membrane filtration zone with an aqueous alkali metal hydroxide solution; and (5) rinsing said crossflow filtration membrane filter with acid on the permeate side after said backwashing, collecting and combining the backwash and rinsing liquids and returning the combined liquids to the input of said plate-type separation zone.

2. The process of claim 1 wherein in step (4) said backwashing is initiated when the transmembranal pressure exceeds 4 bar.

3. The process of claim 1 wherein the membrane in said membrane filtration zone is a ceramic membrane.

4. The process of claim 1 wherein the membrane in said membrane filtration zone is a graphite membrane.

5. The process of claim 1 wherein the membrane in said membrane filtration zone is an aluminum oxide membrane.

6. The process of claim 1 further comprising the steps of: (6) passing said prepurified liquid phase formed in step (1) through a fiber bed separator to form a light phase and a heavy phase; (7) delivering the light phase to the plate-type phase separation zone; (8) passing said heavy phase through said crossflow filtration membrane filtration zone to form a retentate which is returned to the input of said fiber bed separator and a permeate comprised of glycerol and water.

7. The process of claim 6 further comprising a pressure drop through said fiber bed separator which is maintained at a constant value by adjusting the temperature of the inflowing prepurified liquid phase.

8. The process of claim 6 further comprising wherein said prepurified liquid phase formed in step (1) is passed through an adsorption zone containing polyethylene granules as the adsorbent before being passed through said fiber bed separator.

* * * * *

UNITED STATES PATENT AND TRADEMARK OFFICE
CERTIFICATE OF CORRECTION

PATENT NO. : 5,527,974
DATED : Jun. 18, 1996
INVENTOR(S) : Jeromin et al.

It is certified that error appears in the above-indentified patent and that said Letters Patent is hereby corrected as shown below:

On the title page:

Delete the entry "[22] Filed: Sep. 29, 1994" and please add the following PCT information:
PCT Filed: Jan. 27, 1993
PCT No.: PCT/EP93/00184
§ 371 Date: Aug. 5, 1994
§ 102(e) Date: Sep. 29, 1994
PCT Pub. No.: WO93/16025
PCT Pub. Date: Aug. 19, 1993

In Col. 2, line 16, "lowing" should read --flowing--.
In Col. 3, line 25, "AlO$_3$" should read --Al$_2$O$_3$--.
In Col. 5, line 23, "qantity" should read --quantity--.

Signed and Sealed this

Twenty-first Day of April, 1998

Attest:

BRUCE LEHMAN

Attesting Officer

Commissioner of Patents and Trademarks